US008425533B2

(12) United States Patent
Parihar et al.

(10) Patent No.: US 8,425,533 B2
(45) Date of Patent: Apr. 23, 2013

(54) TISSUE RETRIEVAL DEVICE WITH POUCH STRETCHING ARM

(75) Inventors: Shailendra K. Parihar, Mason, OH (US); Frederick E. Shelton, IV, Hillsboro, OH (US); Kevin A. Larson, South Lebanon, OH (US); Wells D. Haberstich, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 414 days.

(21) Appl. No.: 12/693,476

(22) Filed: Jan. 26, 2010

(65) Prior Publication Data

US 2011/0184433 A1 Jul. 28, 2011

(51) Int. Cl.
*A61B 17/22* (2006.01)
(52) U.S. Cl.
USPC ............................................. 606/127
(58) Field of Classification Search .................. 606/110, 606/113, 114, 115, 127, 128, 191, 192, 198, 606/200; 600/184
See application file for complete search history.

(56) References Cited

U.S. PATENT DOCUMENTS

| | | | |
|---|---|---|---|
| 5,190,555 A | 3/1993 | Wetter et al. | |
| 5,215,521 A | 6/1993 | Cochran et al. | |
| 5,320,627 A | 6/1994 | Sorensen et al. | |
| 5,337,754 A | 8/1994 | Heaven et al. | |
| 5,370,647 A | 12/1994 | Graber et al. | |
| 5,465,731 A | 11/1995 | Bell et al. | |
| 5,480,404 A | 1/1996 | Kammerer et al. | |
| 5,524,633 A | 6/1996 | Heaven et al. | |
| 5,647,372 A | 7/1997 | Tovey et al. | |
| 5,649,902 A | 7/1997 | Yoon | |
| 5,735,289 A | 4/1998 | Pfeffer et al. | |
| 5,769,794 A | 6/1998 | Conlan et al. | |
| 5,779,716 A | 7/1998 | Cano et al. | |
| 5,836,953 A | 11/1998 | Yoon | |

(Continued)

FOREIGN PATENT DOCUMENTS

DE DE 92 18 154 9/1993
DE 10 2008 019497 10/2009

(Continued)

OTHER PUBLICATIONS

International Search Report dated Apr. 4, 2011 for Application No. PCT/US2011/021817.

(Continued)

*Primary Examiner* — Ryan Severson
*Assistant Examiner* — Jonathan W Miles
(74) *Attorney, Agent, or Firm* — Frost Brown Todd LLC

(57) ABSTRACT

A tissue retrieval device comprises a tissue retrieval bag and resilient arms. The bag is releasably engaged with the resilient arms. One or two resilient arms expand the bag along a first plane to open the mouth of the bag. Another resilient arm expands the bag along a second plane to unfurl the bag. The first plane is substantially perpendicular to the second plane. The device further comprises a support tube having a passageway and a push/pull rod slidingly positioned within the passageway. The resilient arms are engaged with the push/pull rod such that the resilient arms and the push/pull rod travel uniformly relative to the longitudinal axis of the support tube. The arms collapse within the support tube and are resiliently biased to extend outwardly when the push/pull rod is translated distally relative to the support tube to expose the bag and arms.

20 Claims, 16 Drawing Sheets

U.S. PATENT DOCUMENTS

| | | | |
|---|---|---|---|
| 5,971,995 | A | 10/1999 | Rousseau |
| 6,409,733 | B1 | 6/2002 | Conlon et al. |
| 6,673,080 | B2 | 1/2004 | Reynolds et al. |
| 7,691,111 | B2 | 4/2010 | Bates et al. |
| 7,762,959 | B2 | 7/2010 | Bilsbury |
| 8,016,771 | B2 | 9/2011 | Orban, III |
| 2004/0138587 | A1 | 7/2004 | Lyons, IV |
| 2005/0267492 | A1 | 12/2005 | Poncet et al. |
| 2006/0200170 | A1 | 9/2006 | Aranyi |
| 2006/0247663 | A1 | 11/2006 | Schwartz et al. |
| 2007/0088370 | A1 * | 4/2007 | Kahle et al. .......... 606/114 |
| 2011/0184311 | A1 | 7/2011 | Parihar et al. |
| 2011/0184430 | A1 | 7/2011 | Parihar et al. |
| 2011/0184431 | A1 | 7/2011 | Parihar et al. |
| 2011/0184432 | A1 | 7/2011 | Parihar et al. |
| 2011/0184433 | A1 | 7/2011 | Parihar et al. |
| 2011/0184434 | A1 | 7/2011 | Parihar et al. |
| 2011/0184435 | A1 | 7/2011 | Parihar et al. |
| 2011/0184436 | A1 | 7/2011 | Shelton, IV et al. |

FOREIGN PATENT DOCUMENTS

| | | |
|---|---|---|
| EP | 0 578 997 | 1/1994 |
| EP | 0 950 376 | 10/1999 |
| WO | WO 93/15671 | 8/1993 |
| WO | WO 95/09666 | 4/1995 |
| WO | WO 98/38920 | 9/1998 |
| WO | WO 01/10308 | 2/2001 |
| WO | WO 2005/112783 | 12/2005 |

OTHER PUBLICATIONS

International Search Report dated Apr. 19, 2011 for Application No. PCT/US2011/021046.

International Search Report and Written Opinion dated Aug. 1, 2011 for Application No. PCT/US2011/021042.

International Search Report dated Oct. 11, 2011 for Application No. PCT/US2011/021049.

* cited by examiner

TISSUE RETRIEVAL DEVICE WITH POUCH STRETCHING ARM

BACKGROUND

Endoscopic surgery (e.g., laparoscopy) is a procedure wherein surgery is performed through a series of small openings or incisions in a patient. This type of surgery may reduce or eliminate the need for large incisions and may change some otherwise open surgical procedures such as gall bladder removal to simple outpatient surgery. Consequently, the patient's recovery time may change from weeks to days. These types of surgeries may be used for repairing defects or for the removal of diseased tissue or organs from areas of the body such as the abdominal recess. In some of these procedures, biological material or tissue may be removed or excised from the body through a small opening such as an incision, a small natural orifice, or through a small diameter laparoscopic access port such as a trocar.

Various types of tissue retrieval pouches or bags have been developed to allow for the removal of tissue through a small opening, orifice, or port in an endoscopic surgical procedure. Various instruments have also been devised for introducing, opening, positioning, and closing tissue retrieval bags within a patient; and for removing the bags and enclosed tissue from the surgical site. Some exemplary retrieval bags and associated instruments are disclosed in U.S. Pat. No. 5,465,731, entitled "Specimen Retrieval Pouch and Method for Use," issued Nov. 14, 1995, the disclosure of which is incorporated by reference herein; U.S. Pat. No. 5,480,404, entitled "Surgical Tissue Retrieval Instrument," issued Jan. 2, 1996, the disclosure of which is incorporated by reference herein; U.S. Pat. No. 5,647,372, entitled "Specimen Retrieval Pouch and Method for Use," issued Jul. 15, 1997, the disclosure of which is incorporated by reference herein; U.S. Pat. No. 5,971,995, entitled "Surgical Pouch Instrument," issued Oct. 26, 1999, the disclosure of which is incorporated by reference herein; and U.S. Pat. No. 6,409,733, entitled "Specimen Retrieval Bag," issued Jun. 25, 2002, the disclosure of which is incorporated by reference herein.

While a variety of tissue retrieval devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
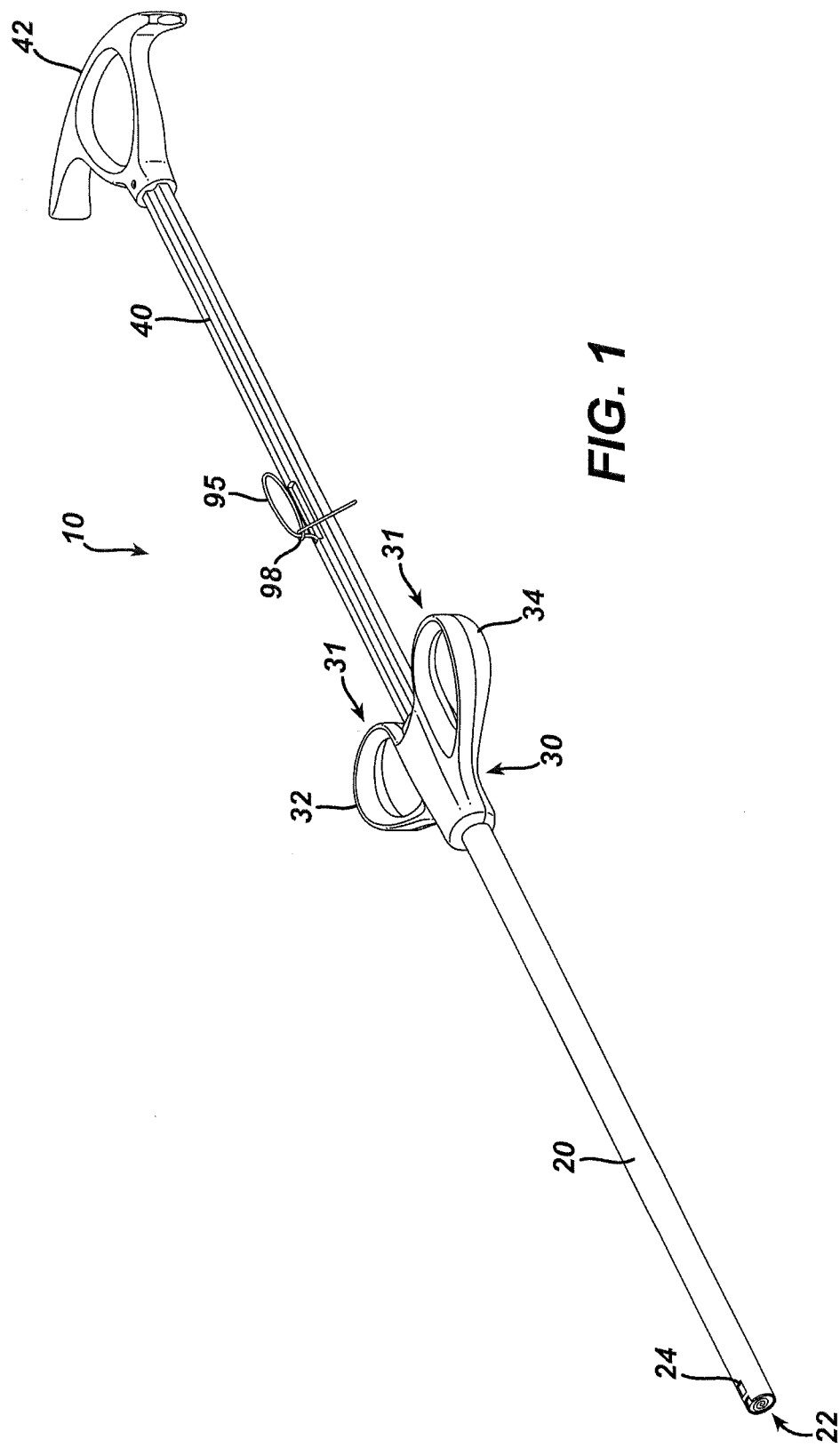
FIG. 1 depicts a perspective view of an exemplary tissue retrieval device in an unactuated configuration.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping tissue retrieval device (10, 210). It will be further appreciated that for convenience and clarity, spatial and directional terms such as "right," "left," "vertical," "horizontal," "clock-wise," and "anti clock-wise" are used herein with respect to the drawings. However, surgical instruments are used in many orientations and positions, and these terms are not intended to be limiting or absolute.

Figure 2:
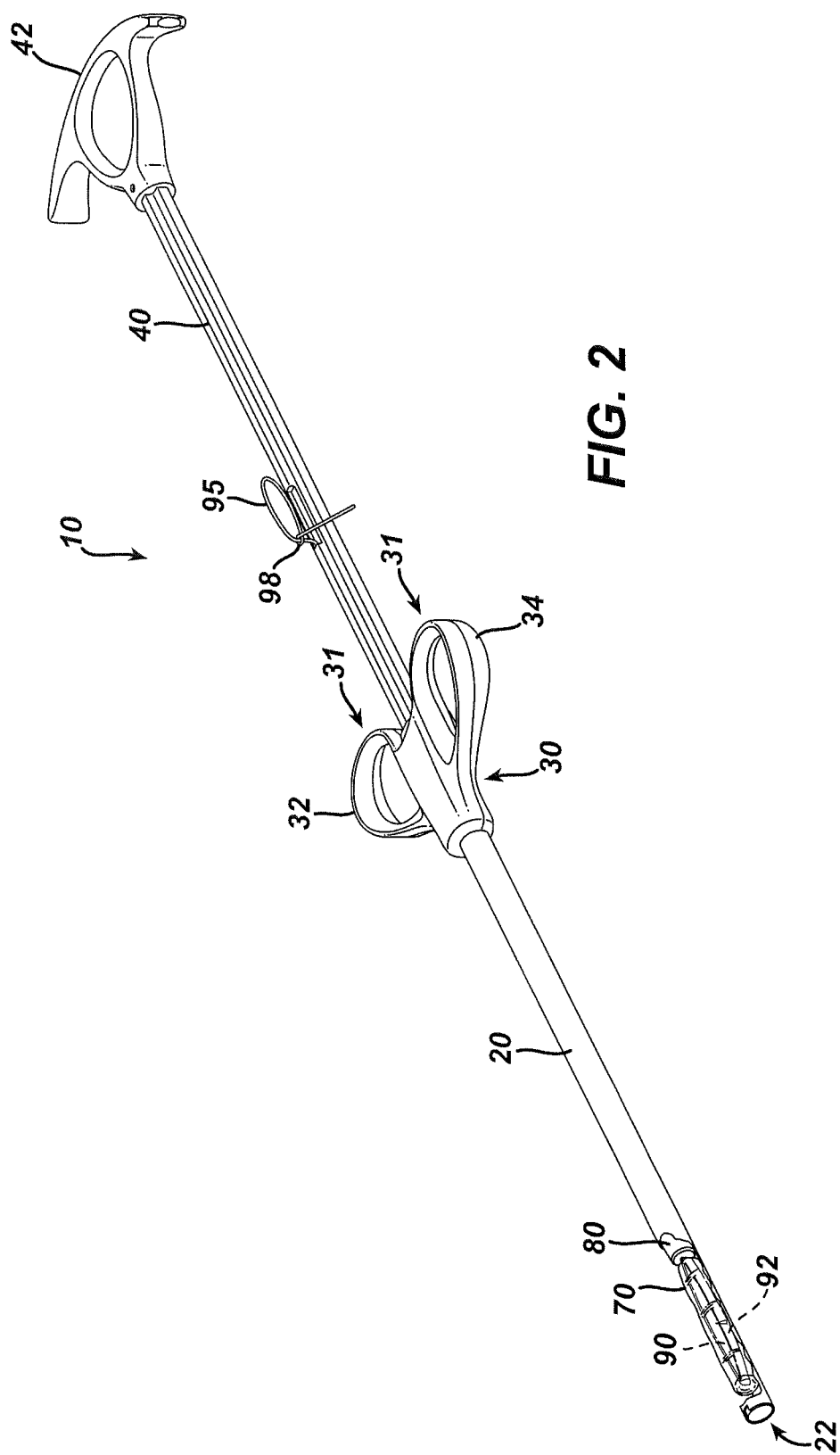
FIG. 2 depicts a perspective view of the tissue retrieval device of FIG. 1 in an unactuated configuration, with a portion of the support tube removed to reveal the tissue retrieval bag and spring arms within the support tube.
Figure 3:
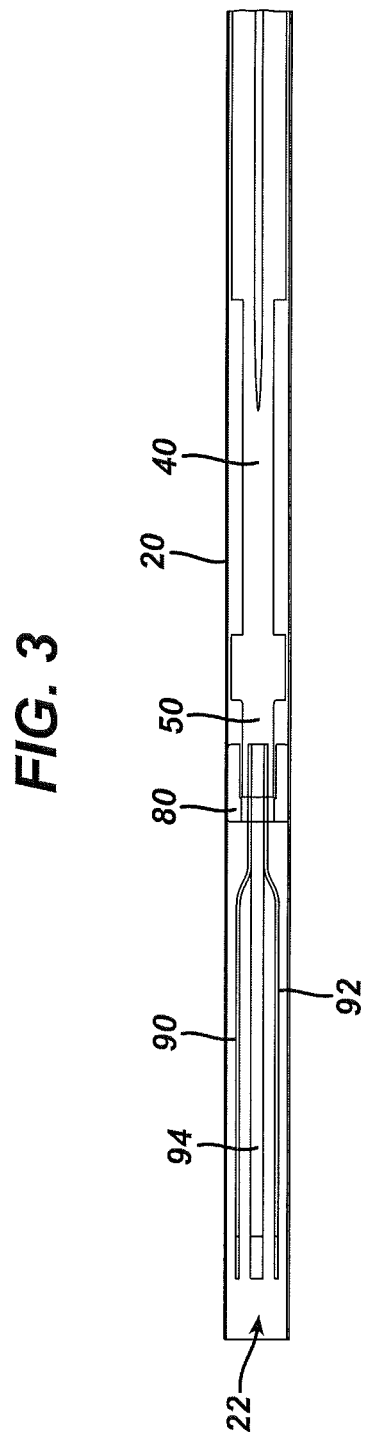
FIG. 3 depicts a partial, top cross-sectional view of the distal portion of the tissue retrieval device of FIG. 1 in an unactuated configuration, without the tissue retrieval bag.

FIGS. 1-11 illustrate an exemplary tissue retrieval device (10) and its associated components. FIGS. 1-3 depict an unactuated tissue retrieval device (10) ready for insertion into a patient. As shown, tissue retrieval device (10) comprises an elongated support tube (20) with a handle (30) at the proximal end. Handle (30) comprises an upper half (32) and a lower half (34) attached to support tube (20). A pair of opposed finger loops (31) extend from handle (30), and an unobstructed lumen or passageway (22) extends through support tube (20) and handle (30). In the present example, an inner rod or push/pull rod (40) is slidingly located within passageway (22) and comprises a thumb ring (42) at a proximal end. Push/pull rod (40) further comprises an attachment portion (50) that engages a plurality of spring arms (90, 92, 94) at a distal end of push/pull rod (40), as will be described in more detail below. The plurality of spring arms (90, 92, 94) may be fixedly engaged with attachment portion (50), although this is not required (e.g., spring arms (90, 92, 94) may instead be movably engaged with attachment portion (50), etc.). In this example, the plurality of spring arms (90, 92, 94) extend distally from attachment portion (50) through a distal plug (80) and releasably engage a tissue retrieval bag (70). Distal plug (80) is configured to releasably receive at least a portion of attachment portion (50), which will be described in more detail below. In FIGS. 1-2, tissue retrieval bag (70) is shown constrained within passageway (22) at the distal end of support tube (20).

Figure 4:
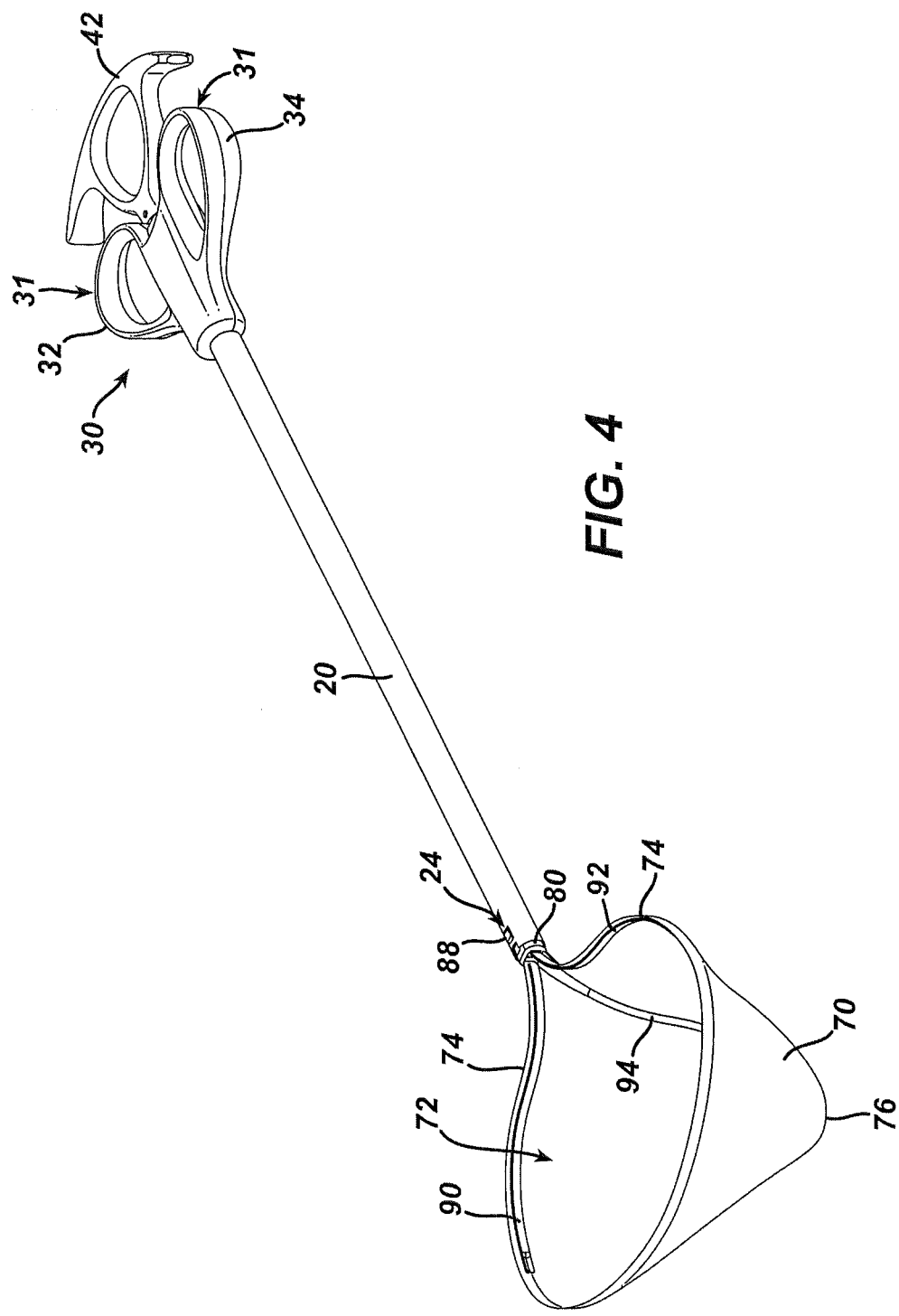
FIG. 4 depicts a perspective view of the tissue retrieval device of FIG. 1 in an actuated configuration.
Figure 5:
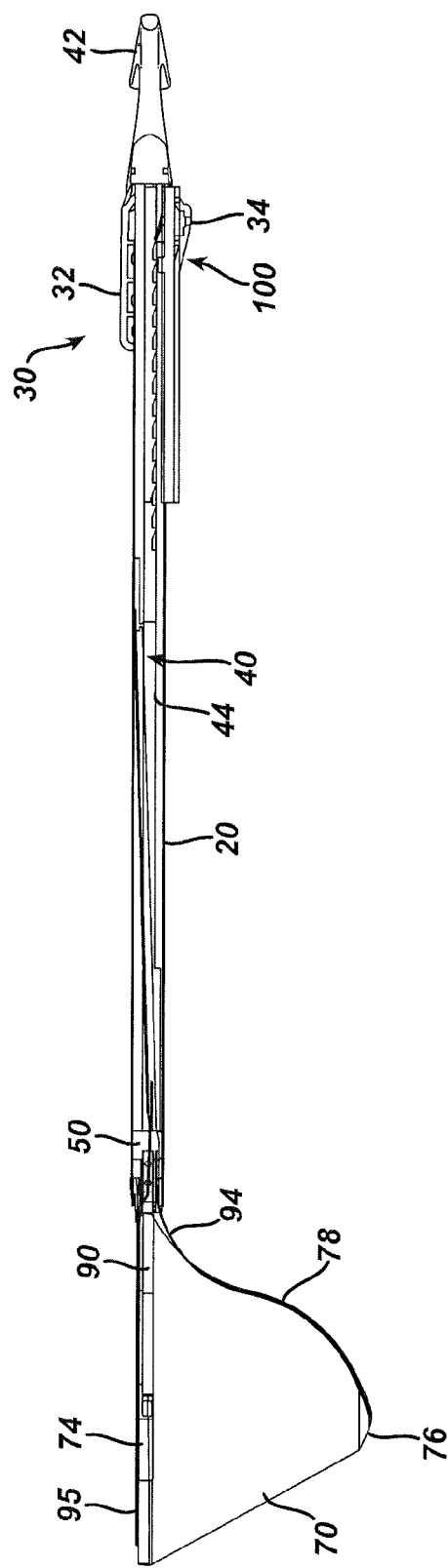
FIG. 5 depicts a side cross-sectional view of the tissue retrieval device of FIG. 1 in an actuated configuration.
Figure 6:
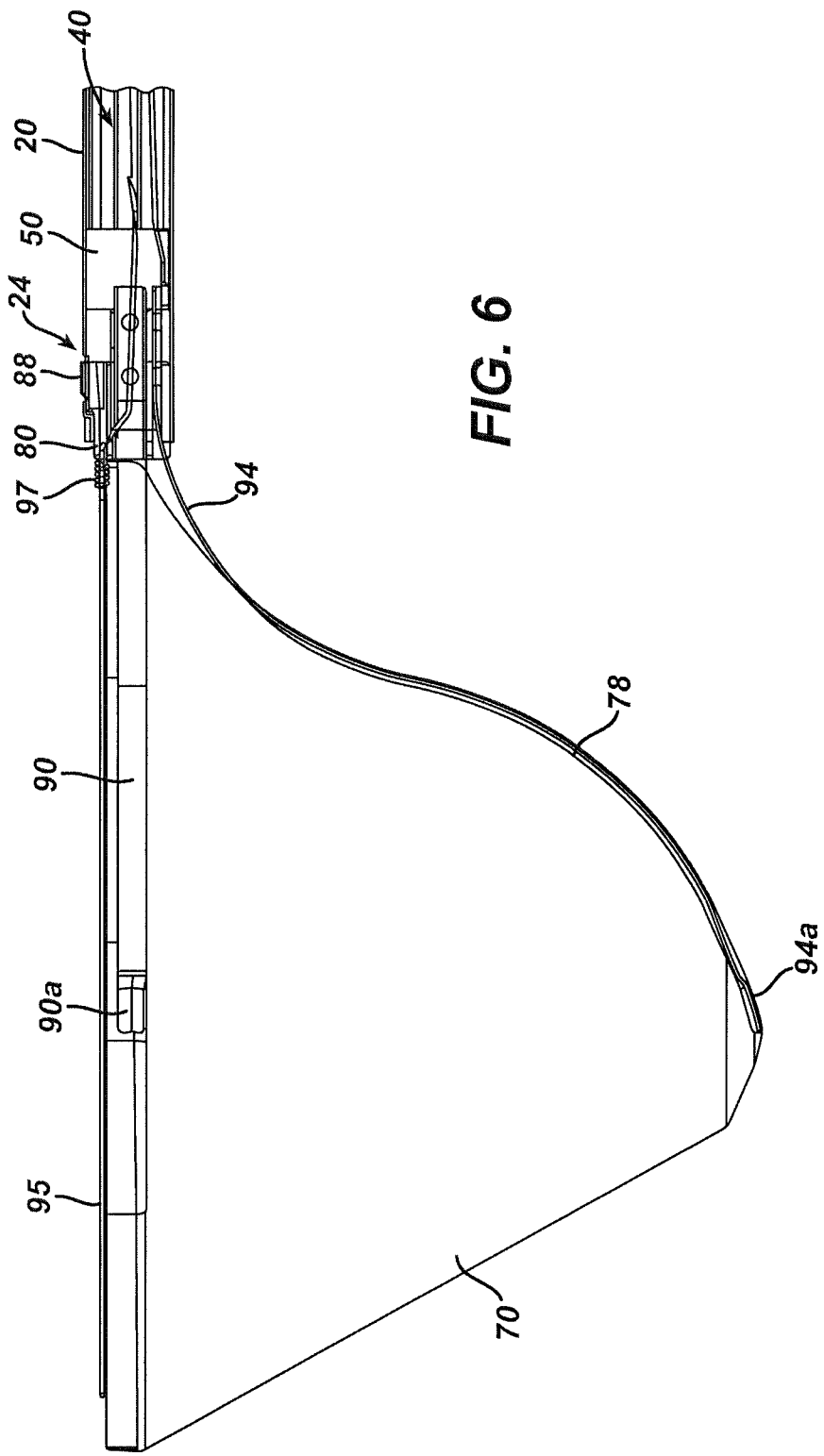
FIG. 6 depicts a partial, side cross-sectional view of the distal portion of the tissue retrieval device of FIG. 1 in an actuated configuration.

FIGS. 4-6 depict tissue retrieval device (10) after the device has been actuated to deploy tissue retrieval bag (70) from the distal end of support tube (20). As shown, push/pull rod (40) has been distally advanced relative to support tube (20) and has pushed tissue retrieval bag (70) from the distal end of support tube (20). Of course, an alternative motion may be proximal retraction of support tube (20) relative to push/pull rod (40). In this example, distally advanced push/pull rod (40) has also locked distal plug (80) into a notch (24) in support tube (20). Such locking engagement between distal plug (80) and support tube (20) may substantially prevent proximal movement of distal plug (80) during subsequent proximal retraction of push/pull rod (40) relative to support tube (20). Of course, some other versions may exclude such locking, and may freely permit proximal retraction of distal plug (80) relative to support tube (20). The plurality of spring arms (90, 92, 94) releasably attach tissue retrieval bag (70) to push/pull rod (40) in the present example.

Figure 8:
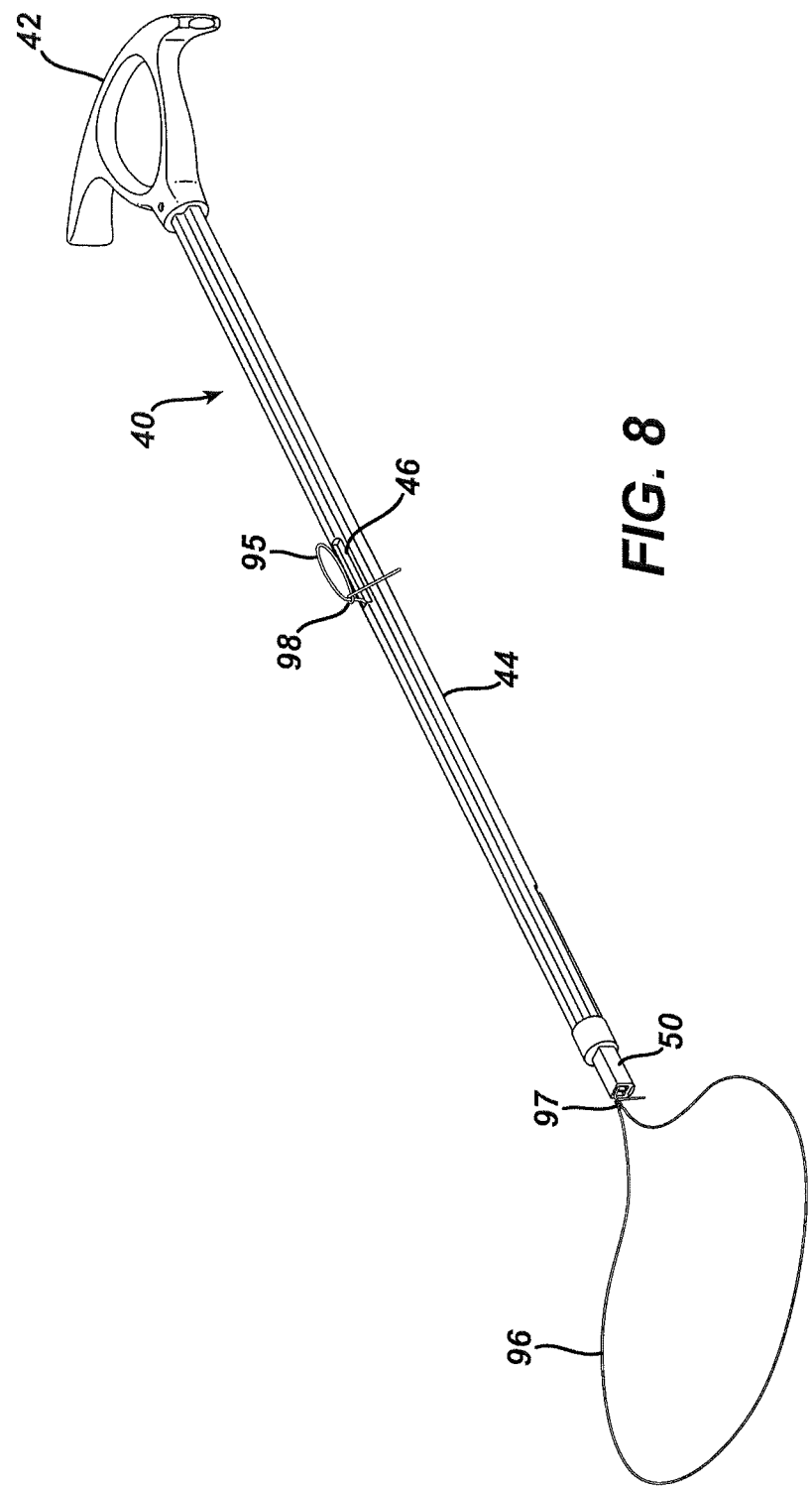
FIG. 8 depicts a perspective view of an exemplary push/pull rod and closure string of the tissue retrieval device of FIG. 1.

In this example, a closure string (95) is releasably engaged with push/pull rod (40) at a proximal end, and distally terminates in a closeable noose (96) extending around the periphery of the mouth (72) of tissue retrieval bag (70). The proximal end of closure string (95) threads through support tube (20), as will be further described below. As shown in FIG. 8, closure string (95) comprises a proximal releasable knot (98) and a distal slip knot (97). Proximal releasable knot (98) is configured to maintain engagement between closure string (95) and push/pull rod (40) until proximal releasable knot (98) is removed by the user. Prior to removal of proximal releasable knot (98), closure string (95) and push/pull rod (40) travel in unison as the user advances or retracts push/pull rod (40). Distal slip knot (97) abuts distal plug (80) and is configured to allow noose (96) to close as push/pull rod (40) and closure string (95) are pulled proximally after tissue retrieval bag (70) has been deployed.

Figure 7:
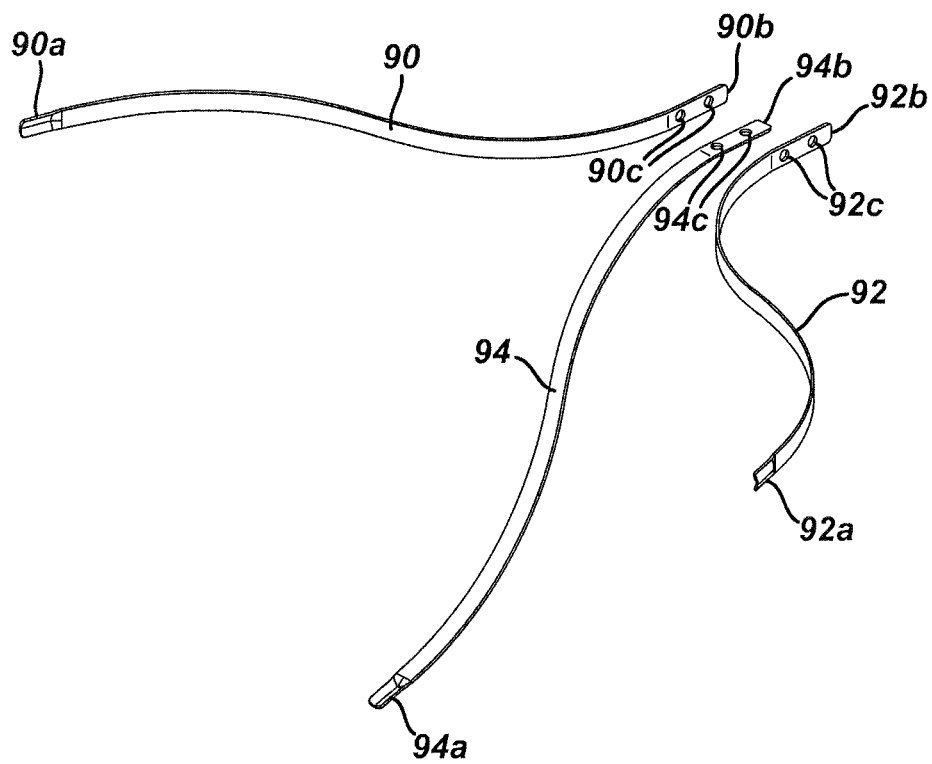
FIG. 7 depicts a perspective view of exemplary spring arms of the tissue retrieval device of FIG. 1, in an actuated configuration.

In the present example, the plurality of spring arms (90, 92, 94) comprises a pair of lateral spring arms (90, 92) and a central spring arm (94). Spring arms (90, 92, 94) may be formed from any suitable material, including but not limited to a resilient material such as stainless steel, nitinol, steel spring alloys, copper spring alloys, plastic, metal reinforced plastic, any other material that can be stored in a deformed shape and return to an initial or near initial shape when released, etc. Alternatively, spring arms (90, 92, 94) may be formed of any other suitable material or combination of materials having any suitable properties. Spring arms (90, 92, 94) may all be made out of the same material, although this is not required. As shown in FIG. 7, the distal tips (90a, 92a, 94a) of each of the spring arms are sized and shaped to increase the grip between tissue retrieval bag (70) and spring arms (90, 92, 94). As shown in FIG. 7, the proximal ends (90b, 92b, 94b) of spring arms (90, 92, 94) each comprise a pair of attachment apertures (90c, 92c, 94c).

As shown in FIGS. 1-3, prior to actuation and deployment, spring arms (90, 92, 94) are retained in a storage configuration confined within support tube (20). As shown in FIGS. 4-6, lateral spring arms (90, 92) may be configured to spread open horizontally as they are released from support tube (20) into a substantially "Y" or "V" shape to open a mouth (72) of tissue retrieval bag (70). As central spring arm (94) is released from support tube (20) upon distal advancement of push/pull rod (40) relative to support tube (20), central spring arm (94) may expand vertically downward relative to the mouth (72) of tissue retrieval bag (70) to vertically stretch tissue retrieval bag (70). In this example, each of the plurality of spring arms (90, 92, 94) comprises an s-shaped profile. Alternatively, each spring arm (90, 92, 94) may have any other suitable profile.

In the present example, spring arms (90, 92, 94) each comprise a single unitary piece of material without joints or breaks. However, in some other versions, one or more of the spring arms may comprise a segmented construction. In some such versions, one or more of the spring arms may comprise a single piece of material incorporating one or more hinges or flex points, including but not limited to living hinges, configured to allow that particular spring arm to transition between the storage configuration and the desired expanded configuration. In some other versions, one or more of the spring arms may comprise at least two separate components hinged or connected together to allow that particular spring arm to transition between the storage configuration and the desired expanded configuration. As yet another merely illustrative alternative, one or more of the spring arms may have hollow portions (e.g., made of a plastic balloon type construction, etc.) that are expandable by receiving some fluid (e.g., air, liquid, etc.) to obtain a desired shape, open retrieval bag (70), and/or expand retrieval bag (70). Still other suitable alternative configurations for spring arms (90, 92, 94) will be apparent to those of ordinary skill in the art in view of the teachings herein.

Tissue retrieval device (10) may be used in conjunction with any suitable type of tissue retrieval bag. By way of example only, tissue retrieval device (10) may be used in conjunction with a known tissue retrieval bag, such as the one disclosed by Conlon et al. in U.S. Pat. No. 6,409,733, which is incorporated herein by reference. In the present example, and as shown in FIGS. 4-6, tissue retrieval bag (70) defines a mouth (72), channels (74) surrounding the periphery of mouth (72), and a bottom portion (76). As shown, channels (74) extend around the entire circumference of mouth (72), however this is not required in all versions. In some versions, channels (74) may extend along only a portion of the circumference of mouth (72). In some other versions, channels (74) may be replaced with one or more pockets or loops of material along the periphery of the mouth (72) configured to slidingly engage lateral spring arms (90, 92). As shown in the illustrated version, channels (74) are configured to slidably receive at least a portion of lateral spring arms (90, 92). Bag (70) of the present example further comprises a central channel (78) that extends along a central portion of the body of tissue retrieval bag (70) toward bottom portion (76). As shown, central channel (78) is configured to slidingly receive central spring arm (94). In the illustrated version, tissue retrieval bag (70) is stretchable, and central spring arm (94) is configured to stretch tissue retrieval bag (70) in a substantially vertical direction during deployment. Alternatively, central spring arm (94) may simply assist in unfurling tissue retrieval bag (70) without necessarily stretching tissue retrieval bag (70). For instance, tissue retrieval bag (70) may be non-stretchable in some versions.

In some alternative versions, the tissue retrieval bag may comprise a central slit instead of a central channel. In some such versions, the central slit may be positioned in a central portion of the tissue retrieval bag and be configured to allow central spring arm (94) to pass through the central slit into the interior cavity of the tissue retrieval bag. In some such versions, central spring arm (94) presses against the interior surface of the tissue retrieval bag during and after deployment to stretch the tissue retrieval bag or assist in unfurling the tissue retrieval bag. In yet another alternative example, the tissue retrieval bag may comprise a pocket or a loop on the bottom portion of the tissue retrieval bag configured to receive the distal end of central spring arm (94). The remaining portion of central spring arm (94) may remain on the exterior of the tissue retrieval bag. In some such versions, as central spring arm (94) expands vertically during deployment, central spring arm (94) presses against the pocket/loop to stretch the tissue retrieval bag or otherwise assist in unfurling the tissue retrieval bag. Still other suitable variations of tissue retrieval bag (70) will be apparent to those of ordinary skill in the art in view of the teachings herein.

As shown in FIG. 5, tissue retrieval device (10) includes a motion limiting mechanism or one way ratchet mechanism (100) that is located within handle (30) and operably engages push/pull rod (40). One way ratchet mechanism (100) is similar to the one way ratchet mechanism described by Conlon et al. in U.S. Pat. No. 6,409,733, the disclosure of which is incorporated herein in its entirety. In the present example, one way ratchet mechanism (100) operates only during the deployment of tissue retrieval bag (70) from support tube (20). In this example, a pawl of one way ratchet mechanism (100) slips along teeth during initial distal advancement of push/pull rod (40) to deploy tissue retrieval bag (70) and locks if the user attempts to proximally retract or withdraw push/pull rod (40) during the initial deployment stroke. As shown, once tissue retrieval bag (70) is fully deployed from the end of support tube (20), the one way ratchet mechanism (100) permanently disengages and permits unrestricted proximal and distal movement of push/pull rod (40). Of course, alternate versions of tissue retrieval device (10) may include any other suitable type of motion limiting mechanism or the motion limiting mechanism may be omitted entirely. In other words, one way ratchet mechanism (100) is merely optional.

As shown in FIGS. 5-6 and 8-9, push/pull rod (40) of the present example comprises an elongated connecting member (44) between attachment portion (50) and thumb ring (42). In the present example, connecting member (44) comprises a substantially t-shaped cross-section. However, it will be appreciated that connecting member (44) may comprise any suitable cross-section, including but not limited to circular, square, rectangular, and triangular. In this version, connecting member (44) comprises a flat (46) (see FIG. 8) to facilitate cutting closure string (95) after tissue retrieval bag (70) has been cinched shut as described below. A through hole (not shown) may be provided proximate to or in flat (46) that is in communication with a closure string channel (not shown) within and along push/pull rod (40) configured to allow closure string (95) to internally pass from the distal end of the device (10) to the proximal end without disturbing the sliding relationship between support tube (20) and push/pull rod (40).

Figure 9:
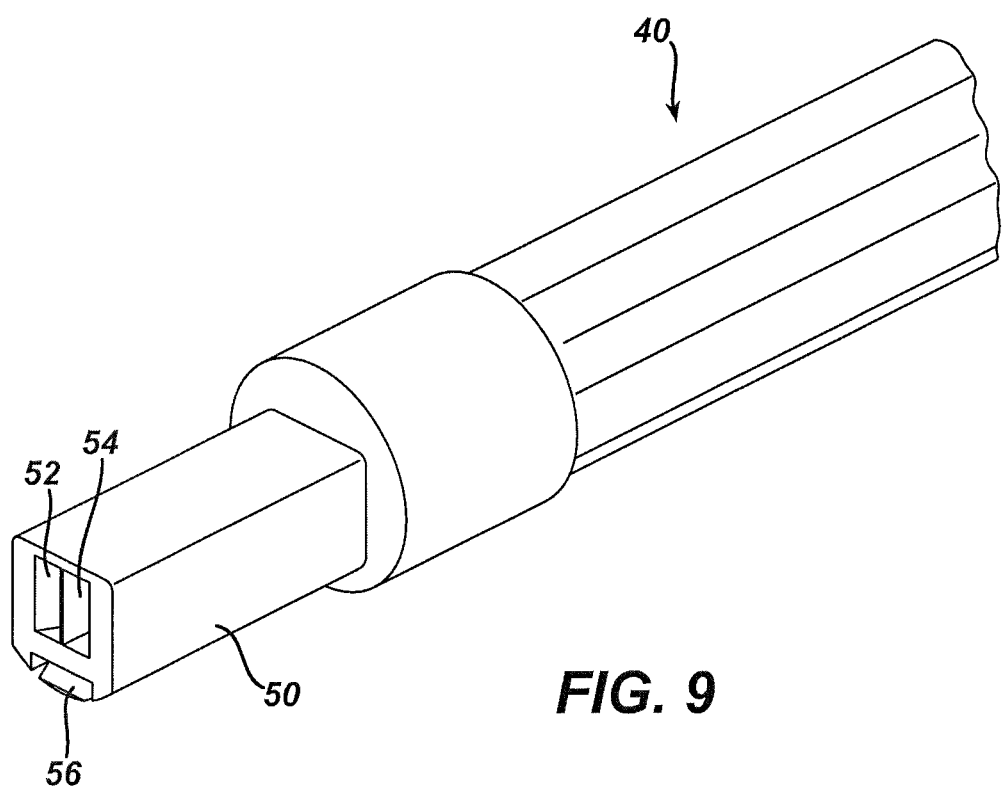
FIG. 9 depicts a partial perspective view of the distal end of the push/pull rod of FIG. 8.

In this example, the distal tip of attachment portion (50) comprises a substantially square cross-section. However, it will be appreciated that the distal tip of attachment portion (50) may comprise any suitable cross-section, including but not limited to circular, rectangular, and triangular, provided at least a portion of the attachment portion may be releasably received by interior cavity (86) of distal plug (80). As shown in FIG. 9, attachment portion (50) comprises a pair of upper spring arm openings (52, 54) and a lower spring arm opening (56) that extend through at least a portion of attachment portion (50). Upper spring arm openings (52, 54) are each configured to receive and engage a proximal end ($90b$, $92b$) of a respective one of lateral spring arms (90, 92), and lower spring arm opening (56) is configured to receive and engage the proximal end ($94b$) of central spring arm (94). Upper spring arm openings (52, 54) and lower spring arm opening (56) are substantially rectangular in the illustrated embodiment. However, upper spring arm openings (52, 54) and lower spring arm opening (56) may comprise any suitable shape configured to receive and engage the proximal end ($90b$, $92b$, $94b$) of a respective spring arm (90, 92, 94). In the present example, attachment portion (50) further comprises a pair of circular attachment members (not shown) in each of upper spring arm openings (52, 54) and lower spring arm opening (56) that are configured to engage attachment apertures ($90c$, $92c$, $94c$) in a respective spring arm (90, 92, 94). Of course, other suitable methods and structures for producing sufficient engagement between spring arms (90, 92, 94) and attachment portion (50) may be used, including but not limited to welding, fasteners, press fitting, and adhesive, etc.

Figure 10:
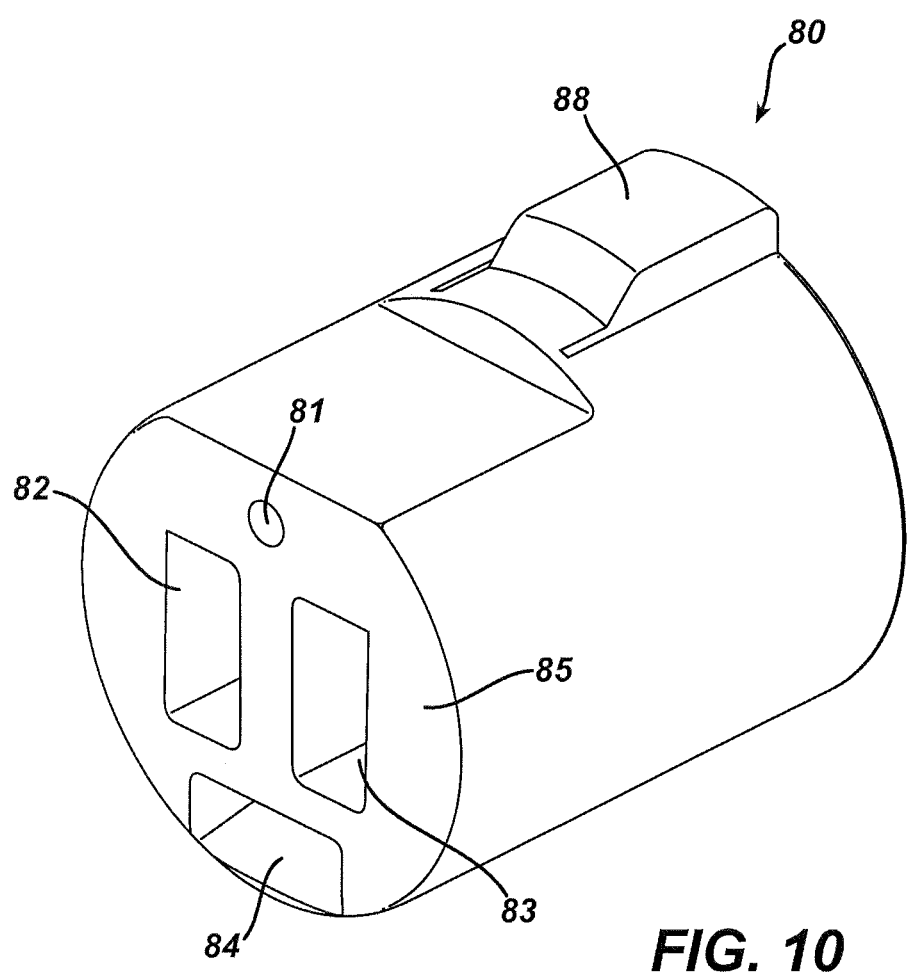
FIG. 10 depicts a front perspective view of an exemplary distal plug.
Figure 11:
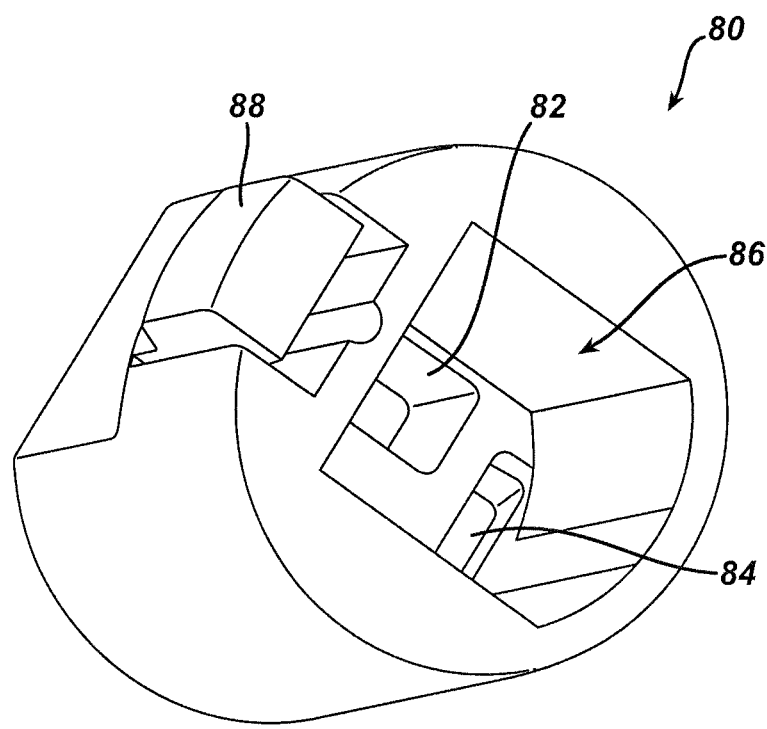
FIG. 11 depicts a rear, perspective view of the distal plug of FIG. 10.

FIGS. 10-11 depict distal plug (80), which comprises a closure string opening (81), a pair of upper openings (82, 83) and a lower opening (84) in the front face (85). As shown, closure string opening (81) is configured to allow closure string (95) to pass through distal plug (80) while preventing distal slip knot (97) from passing therethrough. In this example, upper openings (82, 83) and lower opening (84) are in communication with an interior cavity (86). Upper openings (82, 83) are each configured to be aligned with upper spring arm openings (52, 54) and to slidingly receive a respective one of lateral spring arms (90, 92), and lower opening (84) is configured to be aligned with lower spring arm opening (56) and to slidingly receive central spring arm (94). Upper openings (82, 83) and lower opening (84) are substantially rectangular in the illustrated embodiment. However, upper openings (82, 83) and lower opening (84) may comprise any suitable shape configured to slidingly receive a respective one of spring arms (90, 92, 94). As shown, distal plug (80) further comprises a locking member (88) configured to engage notch (24) in support tube (20). Locking member (88) may flex such that locking member (88) pops through notch (24) during deployment, thereby locking distal plug (80) into position. For instance, locking member (88) may be resiliently biased to an upper position, such that locking member (88) engages notch (24) upon sufficient distal advancement of push/pull rod (40) relative to support tube (20); yet such that locking member (88) may deflect to a lower position to allow distal advancement of push/pull rod (40) from a proximal position. In this example, interior cavity (86) is configured to releasably receive at least a portion of attachment portion (50) of push/pull rod (40). This relationship allows push/pull rod (40) to push distal plug (80) distally as push/pull rod (40) is advanced distally relative to support tube (20); yet also allows push/pull rod (40) to be retracted proximally relative to support tube (20) without pulling on distal plug (80).

In the present example, lateral spring arms (90, 92) and central spring arm (94) are configured to be actuated simultaneously by advancing push/pull rod (40) distally relative to support tube (20), as will be described in more detail below. In some other versions, lateral spring arms (90, 92) and central spring arm (94) may each be configured to be actuated individually. Specifically, some alternative versions may comprise three separate and independently actuatable actuators, where each actuator is associated with a respective spring arm (90, 92, 94). By way of example only, in some such versions, the device may comprise three discrete push/pull rods capable of independent actuation, wherein each of the push/pull rods is associated with a respective spring arm (90, 92, 94).

In some other alternative versions, the pair of lateral spring arms (90, 92) may be configured to be actuated simultaneously with each other, while central spring arm (94) is configured to be actuated independently of the pair of lateral spring arms (90, 92). In some such versions, the device may comprise a first actuator associated with the pair of lateral spring arms (90, 92) and a second actuator associated with central spring arm (94). By way of example only, in some such versions, the device may comprise two discrete push/pull rods capable of independent actuation, wherein the first push/pull rod is associated with the pair of lateral spring arms (90, 92) and the second push/pull rod is associated with central spring arm (94).

In some other alternative versions, the device may comprise a toggle mechanism configured to allow a user to transition between two or more actuation modes, including a first actuation mode, wherein all spring arms (90, 92, 94) are actuated simultaneously together; a second actuation mode, wherein the pair of lateral spring arms (90, 92) are actuated together and central spring (94) arm is actuated independently of the pair of lateral spring arms (90, 92); and a third actuation mode, wherein each of spring arms (90, 92, 94) is actuated independently of the other two spring arms (90, 92, 94).

As yet another merely illustrative variation, spring arms (90, 92) may be substituted with a single unitary hoop. Such a hoop may be resiliently biased to assume a circular or elliptical configuration when push/pull rod (40) is sufficiently advanced distally relative to support tube (20) to open bag (70); while such a hoop may collapse to fit in support tube (20) when push/pull rod is in a proximally retracted position relative to support tube (20). In some such versions, spring arm (94) may still be included to extend in a direction transverse to the plane defined by the hoop, to stretch bag (70) open downwardly or to otherwise assist in the unfurling of bag (70).

These alternative actuation versions may incorporate one or more well known actuators, including but not limited to a button, a trigger, a knob, a slider, and a scissor-type actuator. Still other suitable structures, components, devices, and techniques for actuating spring arms (90, 92, 94) will be apparent to those of ordinary skill in the art in view of the teachings herein.

A merely exemplary method of using tissue retrieval device (10) will now be described. Tissue retrieval device (10) may be used in various types of minimally invasive surgery, including but not limited to endoscopic and laparoscopic procedures. While tissue retrieval device (10) is in an unactuated state, as shown in FIGS. 1-3, the device (10) may be inserted into a patient through a trocar access port to retrieve a sample of excised tissue or other matter. Any suitable conventional trocar access port may be used. By way of example only, support tube (20) may present an outer diameter that is between approximately 5 mm (inclusive) and approximately 15 mm (inclusive) (e.g., approximately 10 mm, etc.). Alternatively, support tube (20) may have any other suitable dimensions.

Once device (10) is sufficiently inserted in the patient, a user may prepare to transition device (10) toward an actuated state by placing his or her thumb into the thumb ring (42) and his or her index and second fingers into the finger loops (31) extending from handle (30). Tissue retrieval bag (70) may be deployed by pushing thumb ring (42) toward handle (30), thereby slidingly advancing push/pull rod (40) distally relative to support tube (20). Before and during the deployment stroke, attachment portion (50) is engaged with interior cavity (86) of distal plug (80) such that attachment portion (50) urges distal plug (80) distally as push/pull rod (40) travels distally. As tissue retrieval bag (70) is ejected from support tube (20) spring arms (90, 92, 94) begin to expand simultaneously in their respective directions to open tissue retrieval bag (70). Specifically, lateral spring arms (90, 92) are resiliently biased to expand in opposite directions in a substantially horizontal plane, thereby opening mouth (72) of tissue retrieval bag (70). Central spring arm (94) is resiliently biased to expand in a substantially vertical plane, thereby stretching or otherwise unfurling bottom portion (76) tissue retrieval bag (70) substantially perpendicularly away from mouth (72) to fully expand tissue retrieval bag (70). In the present example, one way ratchet mechanism (100) prevents proximal movement of push/pull rod (40) relative to support tube (20) until the deployment stroke has been completed.

Upon completion of the deployment stroke, distal plug (80) is locked into position at the distal end of support tube (20) via engagement between locking member (88) and notch (24). Additionally, mouth (72) of tissue retrieval bag (70) is open upon completion of the deployment stroke. The user may then place the targeted tissue sample or other matter into tissue retrieval bag (70) with a conventional grasping instrument or other type of device. Next, the user may simultaneously close tissue retrieval bag (70) and release it from spring arms (90, 92, 94) by pulling thumb ring (42) and retracting push/pull rod (40) proximally relative to support tube (20). As push/pull rod (40) is pulled proximally, tissue retrieval bag (70) abuts distal face (85) of distal plug (80), which provides sufficient resistance to allow spring arms (90, 92, 94) to slide out of each of their respective channels (74, 78). In addition, as push/pull rod (40) is pulled proximally, attachment portion (50) disengages from distal plug (80) and spring arms (90, 92, 94) are retracted through upper openings (82, 83) and lower opening (84) in distal plug (80) into support tube (20). Once spring arms (90, 92, 94) are retracted through distal plug (80), they are disengaged from tissue retrieval bag (70) and return to a substantially straight or compressed configuration within support tube (20), similar to the configuration prior to deployment (as shown in FIG. 3).

As push/pull rod (40) is retracted relative to support tube (20), closure string (95) is also pulled proximally through distal slip knot (97) to close noose (96), which forces mouth (72) of tissue retrieval bag (70) to close. In some versions of removal, the trocar, device (10) and tissue retrieval bag (70) are removed from the patient together through the trocar incision or access site. In some such versions, closure string (95) remains engaged with push/pull rod (40). Device (10) is pulled out of the trocar until the leading edge of tissue retrieval bag (70) is inside the tip of the trocar. Device (10) and the trocar, may then be grasped and removed through the access site together, along with tissue retrieval bag (70).

In some alternate methods of removal, tissue retrieval bag (70) may be disengaged from push/pull rod (40), and the trocar, device (10), and tissue retrieval bag (70) may be removed individually or in an alternate combination. To disengage tissue retrieval bag (70) from device (10), push/pull rod (40) may be retracted a sufficient distance to expose flat (46) and the free end of closure string (95) with proximal releasable knot (98). Distal slip knot (97) is prevented from moving proximally by distal face (85) of distal plug (80) and the relatively narrow inner diameter of closure string opening (81). Once tissue retrieval bag (70) is detached from spring arms (90, 92, 94), tissue retrieval bag (70) remains attached to closure string (95). Closure string (95) may be detached from push/pull rod (40) outside of the patient by releasing proximal releasable knot (98) or cutting closure string (95) below proximal releasable knot (98), perhaps using flat (46) like a cutting board.

Disengaging tissue retrieval bag (70) from device (10) may allow device (10) to be removed from the trocar while tissue retrieval bag (70) remains in the body, cavity with closure string (95) being accessible through the trocar. After device (10) has been removed, tissue retrieval bag (70) may be removed with the trocar by pulling on the free end of closure string (95) until the leading edge of tissue retrieval bag (70) is inside the tip of the trocar. The trocar and tissue retrieval bag (70) may then be removed together through the access site. Alternatively, the trocar may be removed through the access site first, and the user may then remove tissue retrieval bag (70) by pulling on the free end of closure string (95) until tissue retrieval bag (70) passes through the access site. Still other alternative methods of removing device (10) and/or tissue retrieval bag (70), either together or separately, will be apparent to those of ordinary skill in the art based on the disclosure herein.

Figure 12:
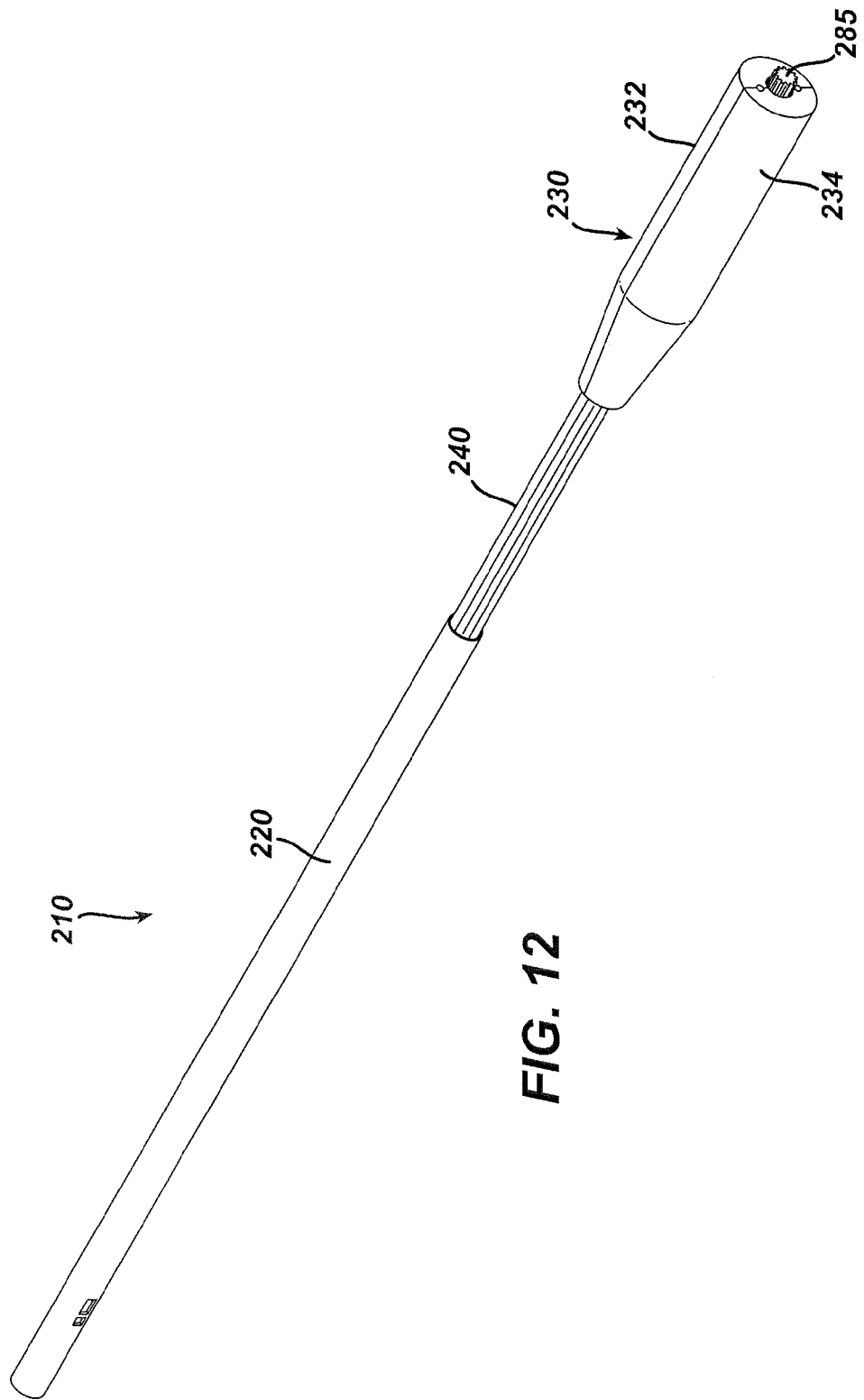
FIG. 12 depicts a perspective view of an exemplary alternative tissue retrieval device in an unactuated configuration.
Figure 13:
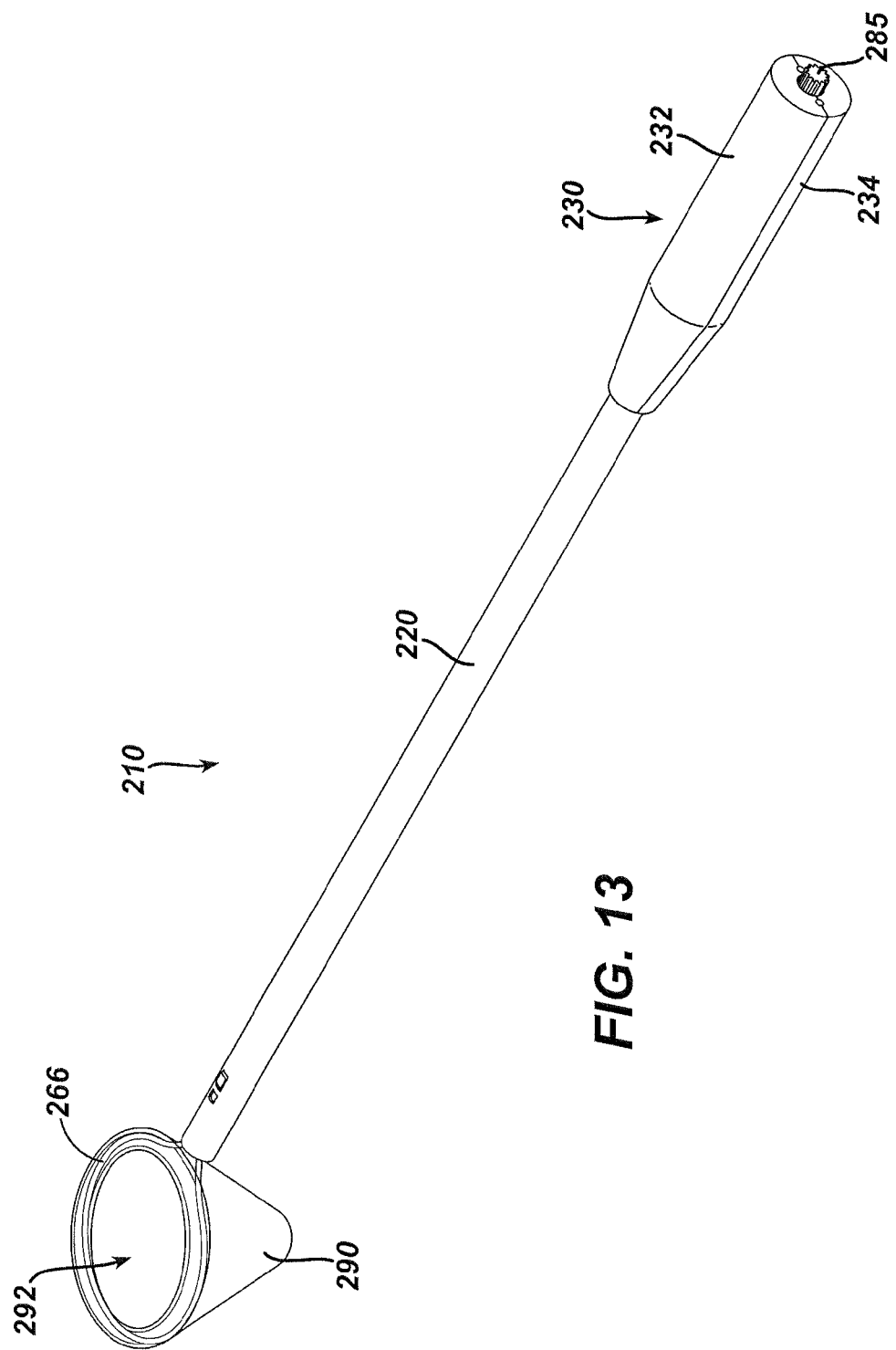
FIG. 13 depicts a perspective view of the tissue retrieval device of FIG. 12 in an actuated configuration.
Figure 14:
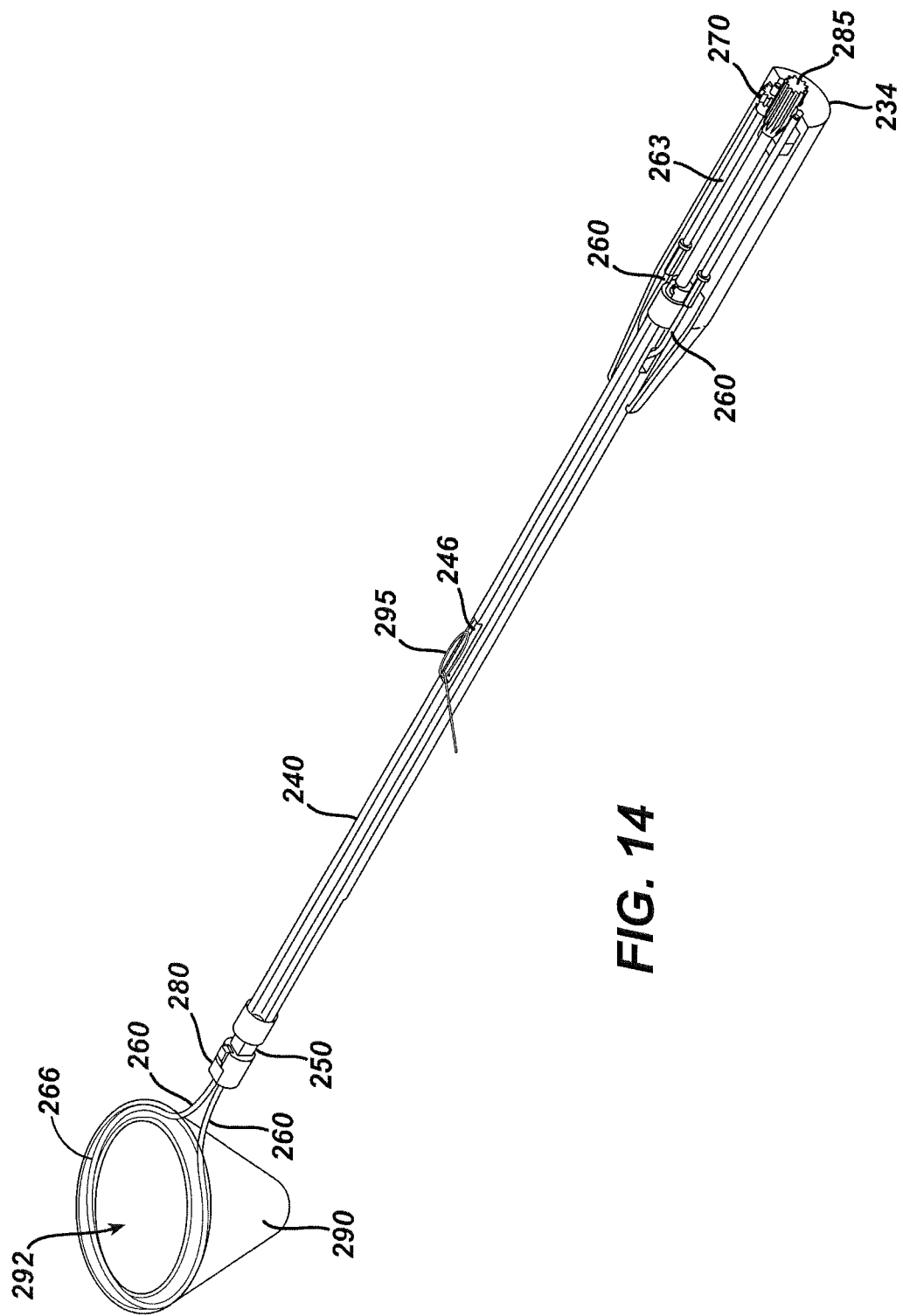
FIG. 14 depicts a perspective view of the tissue retrieval device of FIG. 12 in an actuated configuration, with the support tube and the upper half of the handle removed.
Figure 15:
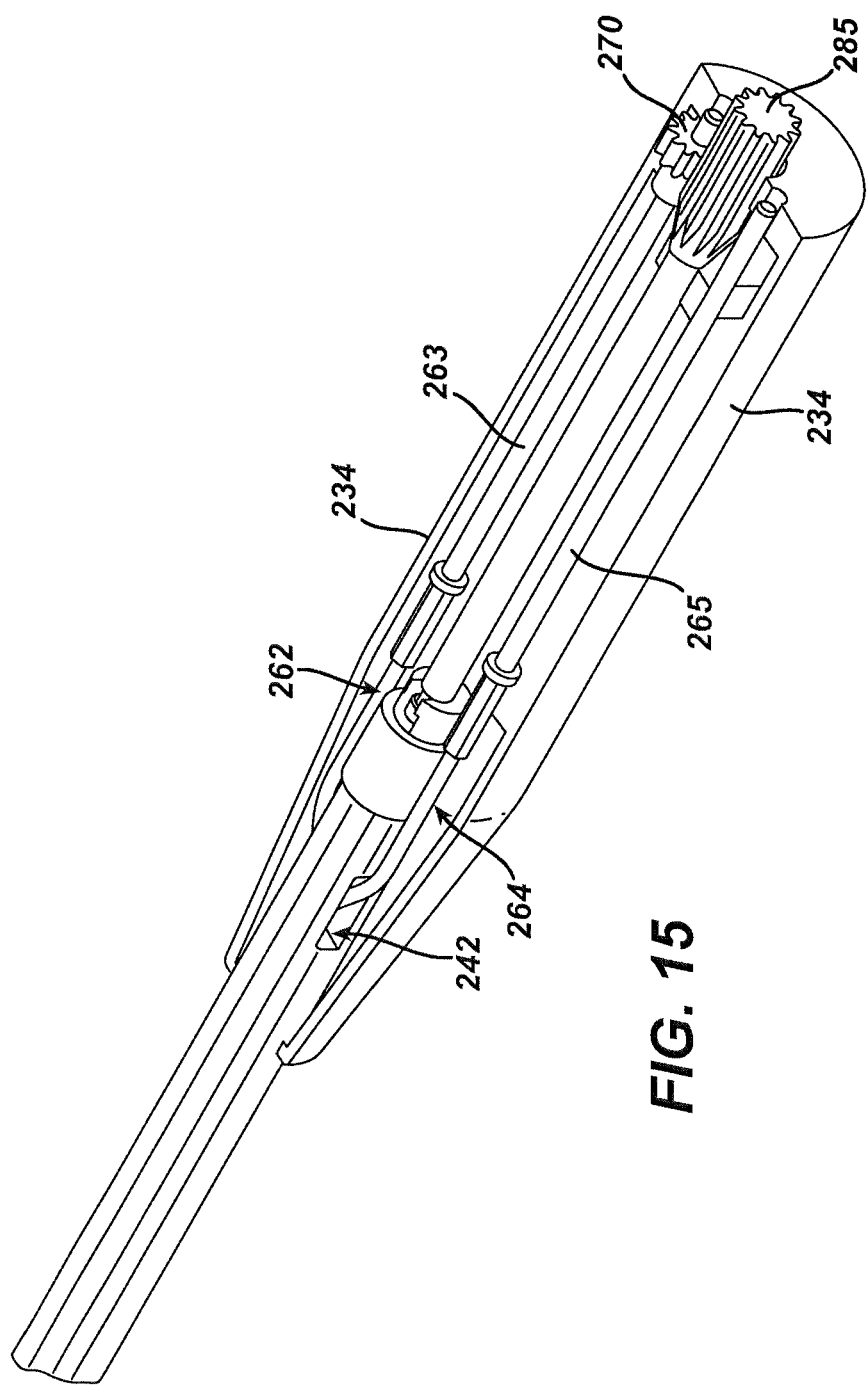
FIG. 15 depicts a partial perspective view of the handle portion of the tissue retrieval device of FIG. 12, with the upper half of the handle removed.
Figure 16:
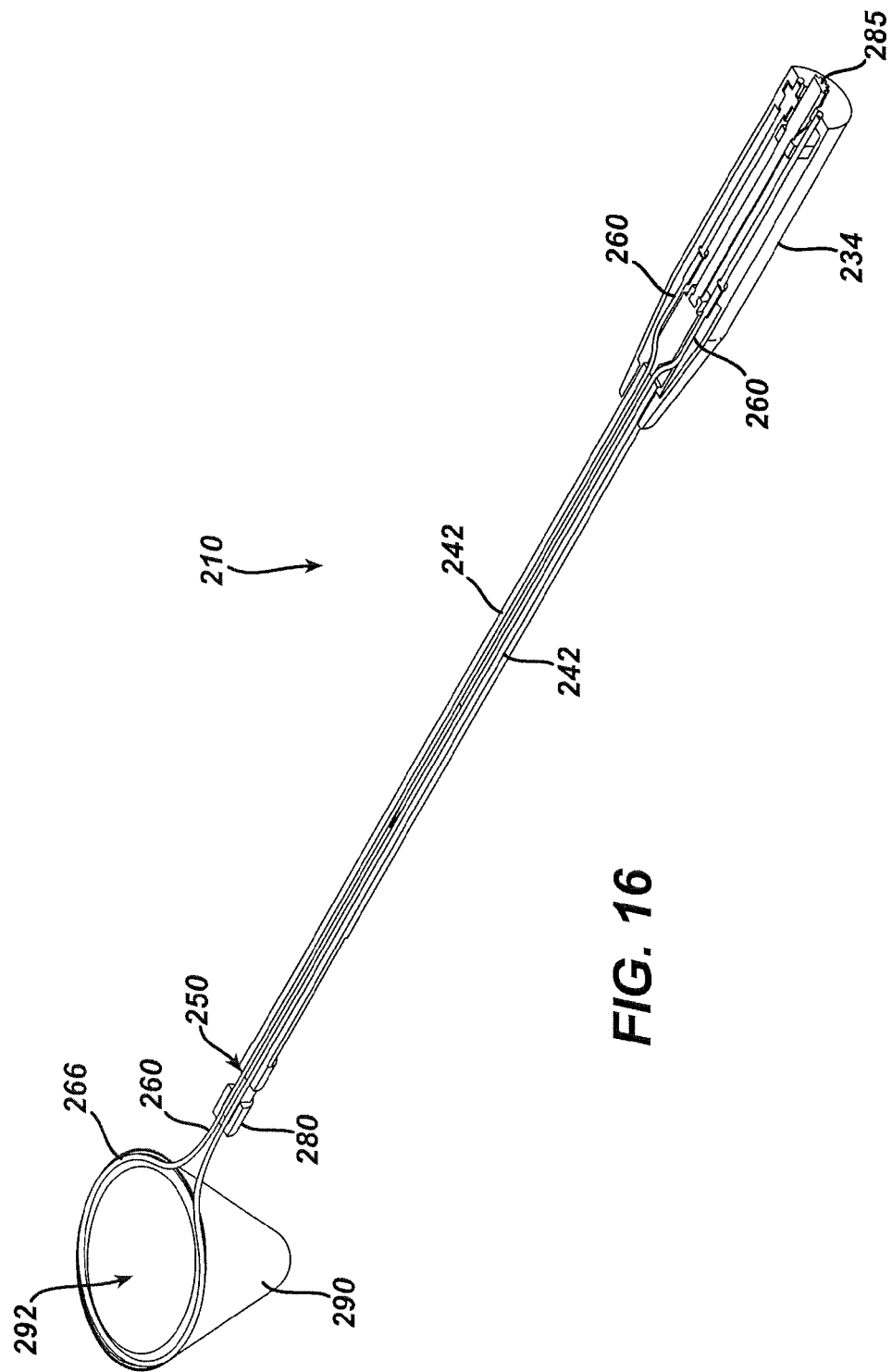
FIG. 16 depicts a perspective, cross-sectional view of the tissue retrieval device of FIG. 12 in an actuated configuration.

FIGS. 12-16 illustrate an exemplary alternative tissue retrieval device (210). FIG. 12 depicts an un-actuated tissue retrieval device (210) ready for insertion into a patient. As shown, tissue retrieval device (210) comprises an elongated, hollow support tube (220), a push/pull rod (240) slidingly located within support tube (220), and a handle (230) attached to the proximal end of push/pull rod (240). Handle (230) comprises an upper half (232) and a lower half (234). The distal end of push/pull rod (240) comprises an attachment portion (250) that releasably engages a distal plug (280) during the deployment stroke. In this example, device (210) further comprises a torsional member (260) engaged with tissue retrieval bag (290). Torsional member (260) may be configured to transition tissue retrieval bag (290) between a deployed state and an undeployed state. As shown, device (210) further comprises a primary gear (285) that is in mechanical communication with torsional member (260) via a secondary gear (270) and a gear shaft (263). Primary gear (285) may extend proximally from handle (230) such that a user may freely grasp and rotate primary gear (285) in either direction, which in turn causes torsional member (260) to simultaneously twist. Of course, a variety of components may be exteriorly coupled with primary gear (285) to assist a user in rotating primary gear (285), including but not limited to a knob or crank, etc.

Torsional member (260) may comprise a wire, a cable or any other suitable type of member. For instance, torsional member (260) may be made up of a flexible material capable of being stored in a deformed shape and expanding to a secondary shape when released. In some versions, torsional member (260) comprises a plurality of segments that are coupled via flexible joints (e.g., "universal joints," etc.). In the present example, torsional member (260) extends along a pair of interior channels (242) formed within push/pull rod (240). A first end (262) and a second end (264) are proximally located within handle (230). First end (262) is engaged with gear shaft (263) and secondary gear (270), and second end (264) is engaged with a gear shaft (265). First end (262) rotates unitarily with gear shaft (263) and secondary gear (270), which also rotates unitarily with primary gear (285). In addition, handle (230), second end (264) of torsional member (260), and gear shaft (265) are all configured to permit second end (264) of torsional member (260) and gear shaft (265) to rotate freely within handle (230). One or more bushings (not shown) may be coupled with gear shaft (265) to facilitate such free rotation. Thus, second end (264) of torsional member (260) rotates concomitantly with first end (262) of torsional member (260).

In the present example, the bent portion of torsional member (260) that extends distally from push/pull rod (240) forms a deformable loop (266) that is engaged with a tissue retrieval bag (290). Deformable loop (266) may be configured to expand into a substantially circular configuration as push/pull rod (240) is pushed distally and deformable loop (266) exits the distal end of support tube (220). Deformable loop (266) may further be configured to contract as push/pull rod (240) is pulled proximally and deformable loop (266) is drawn proximally into support tube (220). In other words, deformable loop (266) of the present example is resiliently biased to assume the configuration shown in FIGS. 13-14 and 16, such as when push/pull rod (240) has been advanced distally relative to support tube (220); while also being collapsible to fit within support tube (220) as shown in FIG. 12, such as when push/pull rod (240) is retracted proximally relative to support tube (220). Still other suitable components, features, configurations, and properties that torsional member (260) may have will be apparent to those of ordinary skill in the art in view of the teachings herein.

In the present example, a closure string (295) is removably engaged with push/pull rod (240) at a proximal end, and distally terminates in a closeable noose (296) extending around the periphery of the mouth (292) of tissue retrieval bag (290). The proximal end of the closure string (295) threads through support tube (220), as will be further described below. As shown, closure string (295) comprises a proximal releasable knot and a distal slip knot, similar to proximal releasable knot (98) and distal slip knot (97) described above. The proximal releasable knot may be configured to maintain engagement between closure string (295) and push/pull rod (240) until the proximal releasable knot is released by the user. Prior to the release of the proximal releasable knot, closure string (95) and push/pull rod (240) travel in unison as the user advances or retracts push/pull rod (240). The distal slip knot may abut distal plug (280) and may be configured to allow noose (not shown) to close retrieval bag (290) as push/pull rod (240) and closure string (295) are pulled proximally after tissue retrieval bag (290) has been deployed.

Push/pull rod (240) of the present example further comprises a flat (246) (see FIG. 14) to facilitate cutting closure string (295) after tissue retrieval bag (290) has been cinched shut as described below. A through hole (not shown) may be provided proximate to or in flat (246) that is in communication with a closure string channel (not shown) within and along push/pull rod (240) configured to allow closure string (295) to internally pass from the distal end of the device (210) to the proximal end without disturbing the sliding relationship between support tube (220) and push/pull rod (240).

Tissue retrieval device (210) may be used in conjunction with any suitable type of tissue retrieval bag. In the present example, tissue retrieval bag (290) defines a mouth (292) configured to receive a tissue sample. In an un-expanded configuration, the bottom of tissue retrieval bag (290) is adjacent to mouth (292). When tissue retrieval bag (290) is fully expanded, the bottom of tissue retrieval bag (290) is displaced from mouth (292) such that tissue retrieval bag (290) may receive a tissue sample therein. Tissue retrieval bag (290) may be wrapped or rolled around torsional member (260) in a rolled/storage configuration such that rotation of torsional member (260) in a first direction unrolls and opens tissue retrieval bag (290). Similarly, rotation of torsional member (260) in a second direction, may roll up tissue retrieval bag (290) about torsional member (260) towards the un-deployed, rolled/storage configuration.

Tissue retrieval device (210) may incorporate a motion limiting mechanism or one way ratchet mechanism, including but not limited to one way ratchet mechanism (100) described above, although this is not required.

A merely exemplary method of using tissue retrieval device (210) will now be described. Tissue retrieval device (210) may be used in various types of minimally invasive surgery, including but not limited to endoscopic and laparoscopic procedures. While tissue retrieval device (210) is in an un-actuated state, as shown in FIG. 12, the device (210) may be inserted into a patient through a trocar access port to retrieve a sample of excised tissue or other matter. Any suitable conventional trocar access port may be used. By way of example only, support tube (220) may present an outer diameter that is between approximately 5 mm (inclusive) and approximately 15 mm (inclusive) (e.g., approximately 10 mm, etc.). Alternatively, support tube (220) may have any other suitable dimensions.

Once device (210) is sufficiently inserted the patient, a user may prepare to transition device (210) toward an actuated state by grasping handle (230) and sliding push/pull rod (240) distally relative to support tube (220). For instance, the user may grip support tube (220) with one hand and grip handle (230) with the other hand to provide such relative sliding. Alternatively, support tube (220) may comprise a hilt-like feature that grounds against the trocar. In some other versions, the user may slide support tube (220) proximally relative to push/pull rod (240) in order to expose deformable loop (266) in the patient (e.g., rather than sliding push/pull rod (240) distally relative to support tube (220), etc.). During the deployment stroke, attachment portion (250) is releasably engaged with distal plug (280) such that attachment portion (250) urges distal plug (280) distally as push/pull rod (240) travels distally. As torsional member (260) and tissue retrieval bag (290) are urged outwardly from the distal end of support tube (220), deformable loop (266) resiliently expands outwardly to open mouth (292) of tissue retrieval bag (290). In the present example, deformable loop (266) expands into a substantially circular configuration, though it should be understood that any suitable configuration may be used (e.g., ovular, elliptical, etc.).

In the present example, upon completion of the deployment stroke, distal plug (280), which may be similar to distal plug (80) described above, is locked into position toward the distal end of support tube (220) via engagement between a locking member on distal plug (280) and a notch in support tube (220). Additionally, mouth (292) of tissue retrieval bag (290) is open upon completion of the deployment stroke. In order to fully deploy tissue retrieval bag (290), the user may rotate primary gear (285) in a first direction. In the present example, rotation of primary gear (285) in the first direction causes secondary gear (270) and torsional member (260) to rotate, thereby deploying tissue retrieval bag (290) by unwinding tissue retrieval bag (290) from its rolled/storage configuration around torsional member (260) toward a fully expanded configuration. Similarly, rotation of primary gear (285) in a second direction may cause secondary gear and torsional member (260) to rotate, thereby contracting tissue retrieval bag (290) by winding tissue retrieval bag (290) up toward its rolled/storage configuration around torsional member (260). By way of example only, the first direction is clockwise and the second direction is counter-clockwise, although the orientation may be reversed in other versions. A conventional grasping instrument or other type of device may be used to facilitate unfurling of tissue retrieval bag (290).

Once tissue retrieval bag (290) has been deployed and expanded, the user may then place the targeted tissue specimen or other matter into tissue retrieval bag (290) with a conventional grasping instrument or other type of device. At this stage, retrieval bag (290) may remain coupled with torsional member (260) and may be removed from the patient by the user pulling proximally on the entire tissue retrieval device (210). Alternatively, retrieval bag (290) may be separated from torsional member (260) within the patient, such that retrieval bag (290) and other parts of tissue retrieval device (210) are removed from the patient separately. It should be understood that there are a variety of ways in which retrieval bag (290) may be released from tissue retrieval device (210).

In some versions, the user continues to rotate primary gear (285) in the first direction until retrieval bag (290) is simply released from torsional member (260). For instance, retrieval bag (290) may be initially wrapped about torsional member (260) in a manner such that friction holds retrieval bag (290) on torsional member (260) when retrieval bag (290) is still substantially wrapped about torsional member (260). In some such versions, tissue retrieval device (210) may include a feature that provides a tactile, audible, and/or visual indication that retrieval bag (290) is near its end of engagement with torsional member, alerting the user to stop rotating primary gear (285) during the retrieval bag (290) deployment stage, to avoid inadvertent separation of retrieval bag (290) from torsional member (260) when retrieval bag (290) is initially being deployed. In addition or in the alternative, tissue retrieval device (210) may include a locking feature that at least temporarily prevents further rotation of primary gear (285) in the first direction when retrieval bag (290) is near its end of engagement with torsional member (260). Such a locking feature may also help avoid inadvertent separation of retrieval bag (290) from torsional member (260) when retrieval bag (290) is initially being deployed. Such a locking feature may also be selectively released by the user when further rotation of primary gear (285) in the first direction is later desired, in order to release retrieval bag (290) from torsional member (260).

As another merely illustrative example, torsional member (260) may be formed of two separable pieces (e.g., left piece and right piece) that are coupled through a conical telescopic joint or other type of coupling at the distal end. After a specimen has been placed in retrieval bag (290), these two separable pieces may be disconnected from each other by pulling on them through some component or feature of handle (230). In some versions of this example, these two pieces are initially inserted through channels formed in retrieval bag (290), allowing the two pieces forming torsional member (260) to hold retrieval bag (290). Thus, as the two separated pieces are pulled proximally, they slip through these channels of retrieval bag (290), thereby releasing retrieval bag (290).

As yet another merely illustrative example, tissue retrieval device (210) is configured to allow one end of torsional member (260) to be pulled proximally through some component or feature of handle (230). In some versions of this example, torsional member (260) is initially inserted through channels formed in retrieval bag (290), allowing torsional member (260) to hold retrieval bag (290). Tissue retrieval device (210) may allow first end (262) of torsional member (260) to be pulled proximally relative to handle (230), resulting in second end (264) of torsional member (260) travelling distally through interior channel (242) then through the channel formed in retrieval bag (290) until retrieval bag (290) is released from torsional member (260).

As still another merely illustrative example, retrieval bag (290) has a first channel for receiving torsional member (260) and a second channel for receiving closure string (295). The first channel may be located above the second channel (e.g., such that the first channel is closer to the mouth (292) of retrieval bag (290), etc.). In some versions of this example, the first channel includes perforations, allowing retrieval bag (290) to be ripped away from torsional member (260) with relative ease, and without damaging any portion of retrieval bag (290) other than the first channel. In some other versions of this example, perforations are provided along retrieval bag (290) in a region between the first and second channels, such that a lower portion of retrieval bag (290) may be ripped away from torsional member (260), leaving the first channel coupled with torsional member (260). In either version, the user may use closure string (295) to close retrieval bag (290) after retrieval bag (290) has been separated from torsional member (260). Also in either version, the perforated regions may be ripped in a variety of ways. For instance, a user may rip retrieval bag (290) at perforated regions using conventional tissue graspers or some other instrument within the patient. In addition or in the alternative, the user may start pulling tissue retrieval device (210) out of a trocar through which tissue retrieval device (210) is inserted, and the difference in size between a filled retrieval bag (290) and the access port opening may provide sufficient resistance to tear retrieval bag (290) at a perforated region during such pulling. Still other various ways in which retrieval bag (290) may be removed from a patient will be apparent to those of ordinary skill in the art in view of the teachings herein.

As noted above, the various versions of specimen retrieval instruments described herein, including but not limited to the various versions of retrieval bags described herein, may be used in a conventional endoscopic procedure that includes the insertion of the introducer tube or other component through a small opening, e.g., an incision, natural orifice, or trocar access port, etc. Of course, specimen retrieval instruments described herein may be used in conjunction with any other suitable surgical or medical procedure, such as endoscopic/laparoscopic procedures, open surgical procedures, or robotic-assisted surgery, etc. Still other various settings and combinations in which specimen retrieval instruments described herein may be used will be apparent to those of ordinary skill in the art in view of the teachings herein.

While several specimen retrieval instruments, and components thereof, have been discussed in detail above, it should be understood that the components, features, configurations, and methods of using the specimen retrieval instruments discussed are not limited to the contexts provided above. In particular, components, features, configurations, and methods of use described in the context of one of the specimen retrieval instruments may be incorporated into any of the other specimen retrieval instruments. One merely exemplary additional feature that may be provided in any of the specimen retrieval instruments described herein includes retrieval bags having various sizes and geometries. For example, some specimen retrieval instruments may be designed with small, medium, or large retrieval bags. Also for example, some tissue retrieval instruments may use retrieval bags having pleats and/or gussets that allow for expansion when holding larger specimens. It should also be understood that any of the specimen retrieval instruments and tissue retrieval bags described herein may be capable of receiving tissue specimens and removing tissue specimens from a patient without such tissue specimens needing to be morcellated or otherwise reduced in size before being received and removed by the specimen retrieval instrument and bag. Still other additional and alternative suitable components, features, configurations, and methods of using the specimen retrieval instruments will be apparent to those of ordinary skill in the art in view of the teachings herein.

Other features and modifications that will be appreciated based on the teachings herein involve methods of attaching a retrieval bag to any of the various arms and loops or other components of a specimen retrieval instrument described above. For example, retrieval bags may be configured with one or more sleeves, slots, pockets, loops, slits, etc., for receiving any of the various arms and loops described above. In other versions, retrieval bags may be connected to any of the various arms, loops, or other components using suitable mechanical or chemical means. It will further be appreciated that in some versions the retrieval bag may be detachable from the other components of the specimen retrieval instrument, while in some other versions the retrieval bag may be inseparable from the specimen retrieval instrument. Still other additional and alternative suitable components, features, configurations, and methods of attaching retrieval bags with the other components of a specimen retrieval instrument will be apparent to those of ordinary skill in the art in view of the teachings herein.

It should also be understood that the components, features, configurations, and methods of use described in the context of one of the retrieval bags may be incorporated into any of the other retrieval bags. One merely exemplary additional feature that may be provided in any of the retrieval bags described herein is one or more weld lines. Such weld lines may be intermittent or continuous along the length of the bag. Such weld lines, offering alternating areas of stiffness along the surface of the bag, may enhance the closure of a bag due to the tendency of areas of lesser stiffness to buckle, deform, or fold. In this way, a retrieval bag may be forced or encouraged to buckle or fold in a desired manner as the bag is closed. Still other additional and alternative suitable components, features, configurations, and methods of using the above-described retrieval devices will be apparent to those of ordinary skill in the art in view of the teachings herein.

While the tissue retrieval instruments of the above-described examples are actuated manually by advancing a thumb ring distally relative to finger rings, retracting a sheath relative to an introducer tube, advancing a slider, or in some other manual fashion, etc., it should be understood that any of the tissue retrieval instruments described herein may instead be actuated in any other suitable fashion. By way of example only, a tissue retrieval instrument may instead be actuated electromechanically (e.g., using one or more electrical motors, solenoids, etc.), pneumatically, and/or hydraulically. Various suitable ways in which such alternative forms of actuation may be provided in a tissue retrieval instrument will be apparent to those of ordinary skill in the art in view of the teachings herein. Similarly, various other suitable ways in which a tissue retrieval instrument may be actuated will be apparent to those of ordinary skill in the art in view of the teachings herein.

It should be understood that any of the retrieval bags described herein may have various types of construction. By way of example only, any of the retrieval bags described herein may be constructed from at least one layer of an elastomeric or polymeric material such as but not limited to polyurethane, polyethylene, polypropelene, polyester (Duralar), Poly-isoprene, silicone, vinyl, or a polytetrafluroethylene (Teflon®). For example, any retrieval bag described herein may comprise a single layer of elastomeric or polymeric material. Alternatively, any retrieval bag described herein may be formed of two or more layers of material. For instance, two or more layers of a retrieval bag wall may be aligned and joined together by adhesives, heat welding, heat staking, RF welding, ultrasonically welding, or other suitable method of attachment. Any retrieval bag described herein may also be cut at an angle to provide a taper or special shapes suitable for specific organs of body (e.g., tissue shapes, etc.), which may facilitate removal of the retrieval bag from a patient. Furthermore, any retrieval bag described herein may incorporate flexible metal meshes, thermoformed plastic meshes, fabrics, or aramid fibers such as Kevlar® for reinforcement. Still other suitable materials that may be used to form retrieval bags as described herein, including combinations of materials, will be apparent to those of ordinary skill in the art in view of the teachings herein. Similarly, various other suitable compositions of the walls of the retrieval bags described herein, including but not limited to various structures, components, and features that may be incorporated into the walls of the retrieval bags described herein, will be apparent to those of ordinary skill in the art in view of the teachings herein.

In any of the above described tissue retrieval instruments, the tissue retrieval bag may include a fold-over flap (not shown) for closing the bag. For instance, such a fold-over flap may be used instead of (or in addition to) using a string to effect closure of the bag. Such a fold-over flap may include an adhesive (e.g., pressure sensitive adhesive, etc.) that substantially keeps the flap in a closed position after the flap has been moved to a closed position. A peel-away strip or similar feature may be used to cover such an adhesive before the flap is closed. A conventional grasping instrument or other type of device may be used to peel the peel-away strip and/or close the flap over the mouth of the bag while the bag is still inside the patient. In some other variations, a tissue retrieval bag may be formed at least in part of a material that provides significant static adhesion or other type of adhesion to itself. For instance, the interior surfaces of the tissue retrieval bag may be configured to adhere to each other and/or to adhere to tissue/objects placed in the bag, to reduce the likelihood of tissue/objects in the bag falling out of the bag. In some such versions, a closure string is omitted. Other suitable variations of a tissue retrieval bag will be apparent to those of ordinary skill in the art in view of the teachings herein.

Versions of the devices disclosed herein have application in conventional endoscopic and open surgical instrumentation as well as application in robotic-assisted surgery.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A tissue retrieval device comprising:
   (a) a tissue retrieval bag;
   (b) a first resilient arm, wherein the first resilient arm is releasably engage with the tissue retrieval bag, wherein the first resilient arm is configured to expand the tissue retrieval bag in a first direction; and
   (c) a second resilient arm, wherein the second resilient arm is releasably engaged with the tissue retrieval bag, wherein the second resilient arm is configured to expand the tissue retrieval bag in a second direction;
   wherein the first direction is substantially perpendicular to the second direction; and wherein the first resilient arm and the second resilient arm together define a resilient frame and wherein at least one of the first resilient arm and the second resilient arm comprises a hollow portion configured to expand upon receipt of at least one of air and liquid.

2. The tissue retrieval device of claim 1, wherein the first resilient arm and the second resilient arm are configured to be simultaneously actuated.

3. The tissue retrieval device of claim 1, further comprising a third resilient arm, wherein the third resilient arm is releasably engaged with the tissue retrieval bag, wherein the third resilient arm is configured to expand the tissue retrieval bag in a third direction, wherein the third direction is substantially co-planar with the second direction.

4. The tissue retrieval device of claim 3, wherein the third resilient arm is configured to be simultaneously actuated with the second resilient arm.

5. The tissue retrieval device of claim 3, wherein the third resilient arm is configured to be simultaneously actuated with the first resilient arm and the second resilient arm.

6. The tissue retrieval device of claim 1, wherein the tissue retrieval bag comprises
   a first channel configured to slidingly receive at least a portion of the first resilient arm, and (ii) a second channel configured to slidingly receive at least a portion of the second resilient arm.

7. The tissue retrieval device of claim 6, wherein the tissue retrieval bag comprises a body and a mouth having a perimeter, wherein the body of the tissue retrieval bag extends from the perimeter of the mouth, wherein the first channel is positioned along at least a portion of the body of the tissue retrieval bag, wherein the second channel extends around at least a portion of the perimeter of the mouth.

8. The tissue retrieval device of claim 7, wherein the first channel is oriented substantially perpendicular to the second channel.

9. The tissue retrieval device of claim 1, further comprising:
   (a) a support tube, wherein the support tube comprises a passageway and a longitudinal axis; and
   (b) a push/pull rod, wherein the push/pull rod is slidingly located within the passageway, wherein the push/pull rod is engaged with the first resilient arm and the second resilient arm such that the push/pull rod, the first resilient arm, and the second resilient arm travel uniformly relative to the longitudinal axis of the support tube.

10. The tissue retrieval device of claim 9, further comprising a motion limiting mechanism comprising a ratchet and pawl assembly and configured to engage the push/pull rod such that distal movement of the push/pull rod is prevented during an initial deployment stroke.

11. The tissue retrieval device of claim 9, further comprising a distal plug, wherein the distal plug is slidingly located within the passageway of the support tube, wherein the distal plug is releasably engaged with a distal end of the push/pull rod.

12. The tissue retrieval device of claim 11, wherein the distal plug comprises:
   (i) at least one upper opening configured to slidingly receive the first resilient arm, and
   (ii) at least one lower opening configured to slidingly receive the second resilient arm.

13. The tissue retrieval device of claim 12, wherein the tissue retrieval bag comprises a mouth having a perimeter, wherein the device further comprises a closure string engaged with the tissue retrieval bag about the perimeter of the mouth, wherein the distal plug further comprises a closure string opening configured to allow the closure string to pass through the distal plug.

14. The tissue retrieval device of claim 11, wherein the support tube comprises a notch, wherein the distal plug comprises a resiliently biased locking member disposed on an exterior surface of the distal plug and configured to engage the notch as the distal plug travels distally during a deployment stroke.

15. The tissue retrieval device of claim 1, wherein the first resilient arm and the second resilient arm each comprise an s-shaped profile when fully expanded.

16. A tissue retrieval device comprising:
   (a) a support tube, wherein the support tube has an internal passageway;
   (b) an inner rod, wherein the inner rod is slidingly located within the passageway;
   (c) a pair of lateral resilient arms, wherein the pair of lateral resilient arms are engaged with a distal end of the inner rod;
   (d) a central resilient arm, wherein the central resilient arm is engaged with the distal end of the inner rod; and
   (e) a tissue retrieval bag, wherein the tissue retrieval bag is releasably engaged with the pair of lateral resilient arms and the central resilient arm;
   wherein the pair of lateral resilient arms and the central resilient arm together define a resilient frame and wherein at least one of the pair of lateral resilient arms and the central resilient arm comprises a hollow portion configured to expand upon receipt of at least one of air and liquid.

17. The tissue retrieval device of claim 16, wherein the tissue retrieval bag comprises an open end and a closed end, wherein the open end comprises a periphery, wherein the pair of lateral resilient arms are engaged with the periphery of the open end of the tissue retrieval bag, wherein the central resilient arm is engaged with the closed end of the tissue retrieval bag.

18. The tissue retrieval device of claim 16, wherein the tissue retrieval bag comprises an interior cavity, wherein the tissue retrieval bag further comprises a slit configured to allow the central resilient arm to pass into the interior cavity to thereby engage the tissue retrieval bag.

19. A tissue retrieval device comprising:
   (a) a handle, wherein the handle comprises a pair of opposed finger loops extending from the handle;
   (b) a support tube, wherein the support tube is attached to the handle;
   (c) a passageway, wherein the passageway extends through the handle and the support tube;
   (d) a push/pull rod, wherein the push/pull rod is slidingly located within the passageway, wherein the push/pull rod comprises a thumb ring at a proximal end;
   (e) at least three arms coupled with the push/pull rod, wherein at least two of the at least three arms are movable in opposite directions within a substantially horizontal plane, wherein at least one of the at least three arms is movable within a substantially vertical plane; and
   (f) a tissue retrieval bag, wherein the tissue retrieval bag is releasably engaged with each of the at least three arms;
   wherein the at least three arms together define a resilient frame and wherein at least one of the at least three arms comprises a hollow portion configured to expand upon receipt of at least one of air and liquid.

20. The tissue retrieval device of claim 19, wherein each arm of the at least three arms is resiliently biased to extend outwardly relative to a longitudinal axis defined by the push/pull rod.

* * * * *